US009339450B2

(12) United States Patent
Thorel et al.

(10) Patent No.: US 9,339,450 B2
(45) Date of Patent: May 17, 2016

(54) INJECTABLE COMPOSITION COMBINING A FILLING AGENT AND A FIBROBLAST GROWTH MEDIUM

(75) Inventors: Jean-Noel Thorel, Paris (FR); Hugues Gatto, Saint Paul de Vence (FR)

(73) Assignee: Jean-Noel Thorel, Paris (FR)

(*) Notice: Subject to any disclaimer, the term of this patent is extended or adjusted under 35 U.S.C. 154(b) by 124 days.

(21) Appl. No.: 13/384,938

(22) PCT Filed: Jul. 6, 2010

(86) PCT No.: PCT/FR2010/051421
§ 371 (c)(1),
(2), (4) Date: Jan. 19, 2012

(87) PCT Pub. No.: WO2011/015744
PCT Pub. Date: Feb. 10, 2011

(65) Prior Publication Data
US 2012/0121534 A1    May 17, 2012

(30) Foreign Application Priority Data

Jul. 27, 2009 (FR) ...................................... 09 55235

(51) Int. Cl.
| | | |
|---|---|---|
| A61K 8/67 | (2006.01) | |
| A61K 8/73 | (2006.01) | |
| A61K 33/00 | (2006.01) | |
| A61L 27/52 | (2006.01) | |
| A61L 27/20 | (2006.01) | |
| A61Q 19/08 | (2006.01) | |
| C08L 5/08 | (2006.01) | |
| A61K 9/00 | (2006.01) | |
| A61K 31/728 | (2006.01) | |
| A61K 45/06 | (2006.01) | |

(52) U.S. Cl.
CPC ................ *A61K 8/735* (2013.01); *A61K 8/675* (2013.01); *A61K 9/0019* (2013.01); *A61K 31/728* (2013.01); *A61K 33/00* (2013.01); *A61K 45/06* (2013.01); *A61L 27/20* (2013.01); *A61L 27/52* (2013.01); *A61Q 19/08* (2013.01); *A61K 2800/91* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,314,872 A | | 5/1994 | Kato et al. |
| 5,366,964 A | * | 11/1994 | Lindstrom et al. ............... 514/57 |
| 6,153,582 A | * | 11/2000 | Skelnik ......................... 424/94.2 |
| 6,432,710 B1 | * | 8/2002 | Boss et al. ..................... 435/366 |
| 6,838,448 B2 | * | 1/2005 | Ponzin ............................. 514/54 |
| 2004/0029229 A1 | | 2/2004 | Reeves et al. |
| 2004/0151703 A1 | * | 8/2004 | Ha et al. ........................ 424/93.7 |
| 2005/0282747 A1 | * | 12/2005 | Clark et al. ...................... 514/12 |
| 2006/0148074 A1 | | 7/2006 | Gorfien et al. |
| 2007/0009882 A1 | * | 1/2007 | Rosenberg ......................... 435/4 |
| 2007/0237750 A1 | | 10/2007 | Naughton |
| 2007/0248559 A1 | * | 10/2007 | Thorel et al. ................. 424/70.14 |

FOREIGN PATENT DOCUMENTS

| | | |
|---|---|---|
| WO | WO-9720859 A1 | 6/1997 |
| WO | WO-2008139122 A2 | 11/2008 |
| WO | WO-2008147817 A2 | 12/2008 |

OTHER PUBLICATIONS

Belford, D.A., et al., "Milk-Derived Growth Factors as Serum Supplements for the Growth of Fibroblast and Epithelial Cells", 1995, In Vitro Cell. Dev. Biol., pp. 752-760.*
Allemann, I.B., et al., "Hyaluronic acid gel (Juvederm) preparations in the treatment of facial wrinkles and folds", 2008, Clin. Int. Aging., pp. 629-634.*
International Search Report for PCT/FR2010/051421 in the French and English languages mailed on Oct. 14, 2011 (12 pages).
Berridge, M. et al. "The Biochemical and Cellular Basis of Cell Proliferation Assays That Use Tetrazolium Salts", Biochemica, No. 4 (1996) pp. 14-19.

* cited by examiner

*Primary Examiner* — Michael G Hartley
*Assistant Examiner* — Lance Rider
(74) *Attorney, Agent, or Firm* — Harris Beach PLLC

(57) ABSTRACT

The invention relates to a composition that can be subcutaneously or intradermally injected, comprising: a filling agent; and a fibroblast growth medium.

9 Claims, 4 Drawing Sheets

INJECTABLE COMPOSITION COMBINING A FILLING AGENT AND A FIBROBLAST GROWTH MEDIUM

CROSS-REFERENCE TO RELATED APPLICATIONS

This application is a national stage application under 35 U.S.C. §371 of PCT Application No. PCT/FR2010/051421, filed Jul. 6, 2010, which claims priority to and the benefit of French patent application no. 0955235, filed Jul. 27, 2009, which is incorporated herein by reference in its entirety.

This invention comes under the development of solutions for injection for treating wrinkles.

It proposes combining a classic filling agent, such as hyaluronic acid, with a fibroblast growth medium, having a well-defined composition which will revitalize the dermis.

PRIOR ART

The skin is a tissue which is continually being renewed and which includes a wide variety of cells and specialized structures. In permanent contact with the environment, the skin forms a protective barrier for the body. In addition, it is involved in many physiological processes which allow the body to maintain a fixed, constant temperature. Moreover, the skin plays an important role in the immune system, which protects the body from disease.

Structurally, the skin consists of three layers:
an outer layer, the epidermis,
an inner layer, the subcutaneous tissue,
and an intermediate layer, commonly referred to as the dermis.

The natural human epidermis consists mainly of three types of cells: a large majority of keratinocytes together with melanocytes and Langerhans cells. The epidermis, as the outer layer, acts as a barrier to external agents.

The epidermis itself has 5 distinct layers; from the deepest to the most superficial these are:
the basal layer or stratum germinativum,
the Malpighian layer or stratum spinosum,
the granular layer or stratum granulosum,
the translucent layer or stratum lucidum, and
the cornified layer or stratum corneum.

The dermis provides the epidermis with a solid support and supplies it with nutrients. Essentially the dermis is composed of fibroblasts and an extracellular matrix (ECM) composed mainly of collagen, elastin and a substance known as the "fundamental substance". All of these components are synthesized by the fibroblasts. Leukocytes, erythrocytes and even tissue macrophages are also found in the dermis. In addition it is crossed by blood vessels and nerve fibres.

The subcutaneous tissue or hypodermis is a layer of adipose and connective tissue which covers the nerves and large blood vessels.

During the ageing process, various characteristic signs appear on the skin, indicating modification in its structure and function. The main signs of skin ageing are the appearance of fine lines and/or wrinkles which increase with age. These wrinkles may be deep, of medium depth or superficial and particularly affect the naso-labial folds, the periorbital area, the contours of the lips, the forehead and the area between the eyebrows (lion wrinkles). These wrinkles and fine lines are seen as a depression or folds on the surface of the skin.

Deep wrinkles are thought to be due to dermo-hypodermal modifications, whereas superficial wrinkles could be explained by dermal and possibly epidermal modifications.

Wrinkles are often due to loss of skin elasticity, in particular, softening of the tissues, as well as to the production of fine lines of different thickness. When the dermis loses its elasticity, it is weakened and begins to form deeper wrinkles. As wrinkles are produced, collagen fibres, responsible for the elasticity and the structure of the skin, lose their characteristics, with overproduction of the metalloproteinase enzymes. This abnormal quantity of enzymes degrades the collagen matrix and thus leads to the production of deep wrinkles. Over the years, the dermis therefore tends to become thinner, in particular its collagen layer.

Other factors, such as free radicals, exposure to the sun, pollution, smoking, alcohol consumption or ozone, may damage the skin, through the same phenomena of activating metalloproteinases and collagen decomposition.

During recent years, the treatment of unattractive skin changes, particularly those related to ageing, has developed rapidly and made enormous progress.

Various treatments have been proposed, particularly the injection of natural or synthetic substances, to remedy skin alterations.

In particular we should mention the use of inactivated botulinum toxin (Botox®) as a local injection and the use of laser techniques, or the use of both techniques together.

An alternative to these technical solutions is the injection of filling products into the dermis, so-called dermal fillers. This filling may be performed using non-resorbable products such as polyacrylamide gels or polymethylmethacrylate (PMMA) particles. However, these compounds can lead to inflammatory or hypersensitivity intolerance reactions.

For these reasons, the use of resorbable products has been considered, such as proteins or lipids. At the present time, the preferred technical solution is to use substances present in their natural state in the human body, such as collagen or hyaluronic acid, which are the basis of the majority of the products currently available on the market.

These resorbable products nevertheless have the disadvantage of being fairly quickly broken down in the organism, which reduces their efficacy and necessitates regularly repeated injections.

An example of a naturally resorbable product is hyaluronic acid, a preferred compound.

It should be mentioned that hyaluronic acid (HA) is a natural constituent of the dermis, where it plays an important role in maintaining hydration and elasticity of the skin. However, it decreases in quantity and quality with age, resulting in drying and thinning of the skin which then wrinkles. Since hyaluronic acid is also very water-soluble and forms high viscosity solutions in water, it is one of the most widely used pharmaceutical products.

At the present time, hyaluronic acid used in pharmaceutical products or medical devices intended for treating wrinkles is available in the form of sodium or potassium hyaluronate gel. Nevertheless, these sodium or potassium hyaluronate gels are fairly rapidly bioresorbable (varying typically between 4 and 6 months), which means that the injections must be repeated at regular close intervals.

To try to increase the length of action of hyaluronic acid, stabilized forms of it have been developed. In particular these are chemically cross-linked HA gels. This cross-linking, via intra- or intermolecular bridging, is thought to increase the time the product persists in the dermis. Alternatively, encapsulating hyaluronic acid has been considered (WO2008/147817).

Moreover, the latest developments concerning filling products have concentrated on combining various active ingredients for this application.

Combining hyaluronic acid, as a mechanical filler, with cutaneous administration of other substances which are active in this context has been envisaged. For example, the document WO2008/139122 combines HA with an inhibitor of hyaluronic acid breakdown acting in vivo, to ensure a certain amount of preservation of the HA molecules injected.

Nevertheless it appears that, despite the different alternatives available on the market, there is still a need to develop technical solutions that ensure effective skin repair, lasting over time and which are as painless as possible for the skin.

DESCRIPTION OF THE INVENTION

Given this situation, the applicant has taken a completely new approach.

While the prior art advocates combining a filling agent, such as hyaluronic acid, with an agent protecting the latter, the present invention intends to act at two distinct levels in order to re-establish good skin appearance, acting in particular therefore against ageing.

This invention concerns a dermatological, cosmetic or therapeutic formulation for injection, combining a 'mechanical' filling agent, known as such, with a fibroblast growth medium.

In practice, this means both acting physically to fill the unevenness or folds that form wrinkles and stimulating the growth of fibroblasts in the dermis. Fibroblasts can also grow within the folds and additionally synthesize substances such as elastin and collagen which contribute to dermal regeneration. In addition, the growth medium is likely to stabilize and protect the present filling agent.

The first component of the combination according to the invention is therefore a mechanical filling agent, the main function of which is to create volume within the wrinkles.

In this context dextran sulphate, elastin, collagen and hyaluronic acid in particular can be mentioned. Synthetic filling agents, such as silicone or polyurethane gels, are also concerned by this invention.

In looking for a technical solution which is as compatible as possible with the skin, the use is preferred of natural polymers present in the skin. This disturbs the composition of the dermis as little as possible and reduces the risk of allergic or inflammatory reactions. To greater advantage the natural polymer is hyaluronic acid.

It is known that hyaluronic acid can occur in different forms: as salts, as derivatives such as esters or amides, as a linear or chemically cross-linked form. All these forms can be envisaged for this invention. While cross-linking increases the lifespan of hyaluronic acid molecules in the organism, this however affects its physical/chemical characteristics, its biological properties and its potential immunogenicity.

In seeking a technical solution which is as neutral as possible for the skin, that is to say, a biomimetic solution, non cross-linked hyaluronic acid and its physiologically acceptable salts are preferred, as this molecule is a natural component of the dermis. By physiologically acceptable salts of hyaluronic acid we mean sodium and potassium salts particularly, as well as blends of them.

The filling agent, preferably hyaluronic acid, forms 0.07 to 3% of the total mass of the composition, more preferably 0.8 to 2.5%.

It should be noted that the degree of cross-linking and the molecular weight of the hyaluronic acid selected may depend on the application targeted, particularly the depth of the wrinkles to be treated.

The second necessary component of the composition according to the invention is a fibroblast growth medium.

For this invention, a fibroblast growth medium is defined as a complete medium not only keeping fibroblasts alive but also stimulating their multiplication. The use of a functional assay of growth can determine whether a given medium is a fibroblast growth medium according to the invention. In particular, a suitable functional assay known to those working in the field is the colorimetric observation of the density of living cells using the WST-1 reagent and reading results at 450 nm (Berridge, M. V. et al. (1996): The Biochemical and Cellular Basis of Cell Proliferation Assays That Use Tetrazolium Salts. Biochemica 4, 15-19.)

An example of a fibroblast growth medium available commercially is DMEM standard culture medium (Sigma) supplemented with 10% by weight of cell growth factor FCS (foetal calf serum).

Generally speaking, such media contain extracts of animal or cellular origin which do indeed stimulate the growth of fibroblasts, but which have the disadvantage of not having a defined composition or of containing untraceable exogenous elements such as FCS, bovine pituitary extracts, the cell growth factors EGF (epidermal growth factor) or FGF (fibroblast growth factors), insulin or cholera toxin, hydrocortisone, piperazine, etc.

Advantageously, the fibroblast growth medium used in this invention does not contain cell growth factors or biological extract of animal or cellular origin, particularly if these factors or extracts are not traced or traceable and/or are not of a defined composition.

The expression "not traced" or "not traceable" means that the source of the biological material in question and/or the treatment undergone by the latter cannot be established or checked.

In practice, the said medium preferably contains no biological extract of animal or cellular origin, no cell compound or growth factor, or hormone.

In a preferred embodiment, a fibroblast growth medium, as compatible as possible with the natural composition of the skin, is introduced by injection into the dermis. This is a medium containing components which are biodermal (naturally contained in the skin), biomimetic and/or biocompatible (biologically mimetic or neutral for the skin).

Such a medium will specifically provide fibroblasts with optimized nutrition in the form of vitamins, trace elements, amino acids, mineral salts, simple sugars (such as glucose, ribose, deoxyribose) and/or complexes (such as HA), and natural growth factors in the form of constituents of nucleic acids (nucleotide bases and pentoses needed to form nucleotides, and nucleosides). Advantageously, it will also have a physiological pH between 6.5 and 7.9, between 7.4 and 7.6 and osmolarity between 280 and 450 mOsm, preferably between 300 and 350 mOsm.

It should be noted that HA can be both a component of the growth medium and a filling agent. The difference is in the form of the HA (necessarily a hyaluronate salt in the medium) and its quantity (much lower quantities in the medium).

According to a particular embodiment, all the components of the medium are present naturally in the skin (dermal components). Nevertheless, to stimulate the growth of fibroblasts, such a medium can be enriched using a substance which is exogenous to the skin but of natural, traceable origin and well defined composition. A substance meeting this definition is for example a mixture of peptides extracted from milk, or an MPC (milk peptide complex), obtained by successive precipitations from milk followed by separation of certain proteins subjected to enzymatic hydrolysis. This substance, in the form of a dehydrated powder, is added advantageously to the medium at between 0.5 and 5 mg/ml, more preferably between 4 and 5 mg/ml.

According to another preferred embodiment, the fibroblast growth medium used in the composition according to the invention contains no EDTA or its salts or lipoic acid as metalloproteinase inhibitors.

As an example, a complex medium meeting such a definition has been developed by the applicant and combines about sixty components in precisely defined quantities as follows:

| NAME ACC. TO THE INTERNATIONAL NOMENCLATURE OF COSMETIC INGREDIENTS (INCI) | FINAL CONCENTRATION Solution 1 X (in mg/l) |
|---|---|
| WATER | q.s. 1 litre |
| SODIUM CHLORIDE | 5000 to 8000 |
| L-GLUTAMINE or L-ALANYL-GLUTAMINE | 100 to 3000 |
| SODIUM BICARBONATE | 0 to 2000 |
| D-GLUCOSE | 2000 to 5000 |
| L-ARGININE HCl | 300 to 500 |
| SODIUM ACETATE | 200 to 450 |
| DISODIUM PHOSPHATE $Na_2HPO4$ | 100 to 1500 |
| L-LEUCINE | 50 to 200 |
| L-SERINE | 50 to 200 |
| MAGNESIUM CHLORIDE $MgCl_2 \cdot 6H_2O$ | 50 to 200 |
| POTASSIUM CHLORIDE | 50 to 200 |
| L-VALINE | 20 to 150 |
| SODIUM PYRUVATE | 10 to 75 |
| L-LYSINE HCl | 10 to 75 |
| L-HISTIDINE HCl·$H_2O$ | 10 to 75 |
| L-CYSTEINE HCl $H_2O$ | 10 to 75 |
| ADENINE (HCl) | 5 to 50 |
| L-THREONINE | 5 to 50 |
| CALCIUM CHLORIDE $CaCl_2 \cdot 2H_2O$ | 0 to 22.5 |
| MYO-INOSITOL | 5 to 50 |
| L-GLUTAMIC ACID | 15 to 75 |
| L-ASPARAGINE $H_2O$ | 15 to 75 |
| L-METHIONINE | 10 to 50 |
| L-TYROSINE $2Na_2$ $2H_2O$ | 10 to 50 |
| L-PHENYLALANINE | 2 to 20 |
| L-TRYPTOPHAN | 2 to 20 |
| L-ALANINE | 5 to 30 |
| GLYCINE | 5 to 30 |
| L-ISOLEUCINE | 5 to 30 |
| L-ASPARTIC ACID | 10 to 50 |
| SODIUM SULPHATE | 1 to 10 |
| FERROUS SULPHATE $FeSO_4 \cdot 7H_2O$ | 1 to 10 |
| FOLIC ACID | 1 to 5 |
| THYMIDINE | 0.1 to 3 |
| CYANOCOBALAMINE | 0.1 to 3 |
| D-CALCIUM PANTOTHENATE | 1 to 5 |
| THIAMINE HCL | 1 to 5 |
| THIOCTIC ACID | 0.1 to 1 |
| ZINC SULPHATE $ZnSO_4 \cdot 7H_2O$ | 0.05 to 0.5 |
| SODIUM SILICATE $NA_2SIO_3 \cdot 4H_2O$ | 0.05 to 0.5 |
| PYRIDOXINE HCL | 0.5 to 3 |
| NIACINAMIDE (NICOTINAMIDE) | 0.5 to 3 |
| RIBOFLAVIN | 0.05 to 0.5 |
| d-BIOTIN | 0.01 to 0.05 |
| COPPER SULPHATE $CuSO_4 \cdot 5H_2O$ | 0 to 0.005 |
| AMMONIUM MOLYBDATE $(NH4)_6Mo_7O_{24}4H_2O$ | 0 to 0.005 |
| AMMONIUM VANADATE $NH_4VO_3$ | 0 to 0.001 |
| MANGANESE CHLORIDE $MnCl_2 \cdot 4H_2O$ | 0 to 0.0001 |
| SODIUM HYALURONATE | 100 to 1000 |
| L-PROLINE | 10 to 100 |
| HYDROXYPROLINE | 10 to 100 |
| ASCORBIC ACID | 0.1 to 10 |
| ADENOSINE | 0.01 to 1 |
| GUANINE | 0.01 to 1 |
| DEOXYRIBOSE | 0.01 to 1 |
| RIBOSE | 0.01 to 1 |
| CHOLINE CHLORIDE | 0 to 3 |
| MPC | 0 to 5000 |

A composition according to the invention may in addition contain other ingredients or excipients, usually used for this application, particularly derivatives or purified fractions of HA. Nevertheless, according to a particular embodiment, the injectable composition consists only of the two components described above.

As already stated, this composition is intended for injection and is therefore akin to an injectable implant.

The implant according to this invention is therefore intended to be injected into the superficial, mid or deep dermis, subcutaneously or intradermally, preferably the face.

According to an advantageous embodiment, the composition is in the form of a gel, because of the application for an injectable form as the object of the invention. Remarkably, this restriction is perfectly compatible with the fibroblast growth media described above, which can be formulated as gels, by incorporating HA, without adding exogenous excipients.

To even greater advantage, the composition is in the form of a monophasic hydrogel, i.e. a hydrogel in a single homogeneous phase. The viscosity of the composition obtained can be adjusted easily, particularly by adapting the composition and the quantity of the filling agent. In the case of hyaluronic acid, adjustments can be made to the concentration, which typically varies between 0.07% and 3% by weight of the composition, and also to its degree of cross-linking or its molecular weight.

The injectable composition according to the invention may also form part of a kit which in addition includes syringes which can contain the said composition. For example these might be single dose syringes of 0.5 to 1.5 ml. In such a kit, the 2 essential components of the composition may be presented as a blend in a single syringe, or in 2 distinct syringes for extemporaneous mixing.

Given the intended treatment, such a composition will be preferably sterilized, cold sterilization preferably being used to avoid denaturing the components. This stage may be performed using a 0.22 μm membrane filtration method for the fibroblast growth medium, and by separate sterilization of the HA using a process known from the person skilled in the art.

Given their complementary mode of action, the two components of the composition according to the invention may be administered simultaneously, separately or spread over time.

As already stated, a composition according to the invention is intended to correct all skin irregularities, and in particular to treat, improve and/or prevent skin ageing. Wrinkles, fine lines, dermal depressions and scars are thus targeted, particularly on areas of the face or forehead marked by expression wrinkles.

It could be used for either cosmetic or therapeutic purposes. Both dermatology and reconstructive surgery are concerned by a composition according to the invention.

In other words, this invention concerns a cosmetic or therapeutic method of treatment consisting of injecting the composition defined in this application. It should be noted that the two essential components of this composition may be blended extemporaneously. In the same way, they do not need to be injected at the same time.

Because of the particular composition according to this invention, two complementary physiological actions are targeted and obtained: firstly, the mechanical filling of irregularities and secondly, an action contributing to cell renewal and through this to the synthesis by the fibroblasts of newly formed components, particularly collagen and elastin. This results in remodelling of the extracellular matrix and revitalization of the dermis.

Thus there is immediate mechanical filling after the injection and ultimately cell regeneration. Decreasing the concentrations of filling agent can therefore be envisaged during the treatment. Indeed, once the growth of fibroblasts takes over, the mechanical filling agent becomes less necessary and, in practice, the quantities of filling agent can be reduced.

Furthermore, in a preferred embodiment, such a composition is completely biocompatible with the skin, in as far as it is essentially composed of components that are naturally present in the dermis. Due to this, the microenvironment of the skin is not disturbed, thus reducing the risks of inflammatory or allergic reactions. Moreover, it has been shown that such biomimetic and biocompatible media allow growth of stimulated fibroblasts in the presence of serum. They are thus particularly suitable candidates for dermal injection since the dermis is richly vascularized.

The invention will now be illustrated by the following non-limiting examples aided by the attached figures.

LEGENDS OF THE FIGURES

Figure 3:
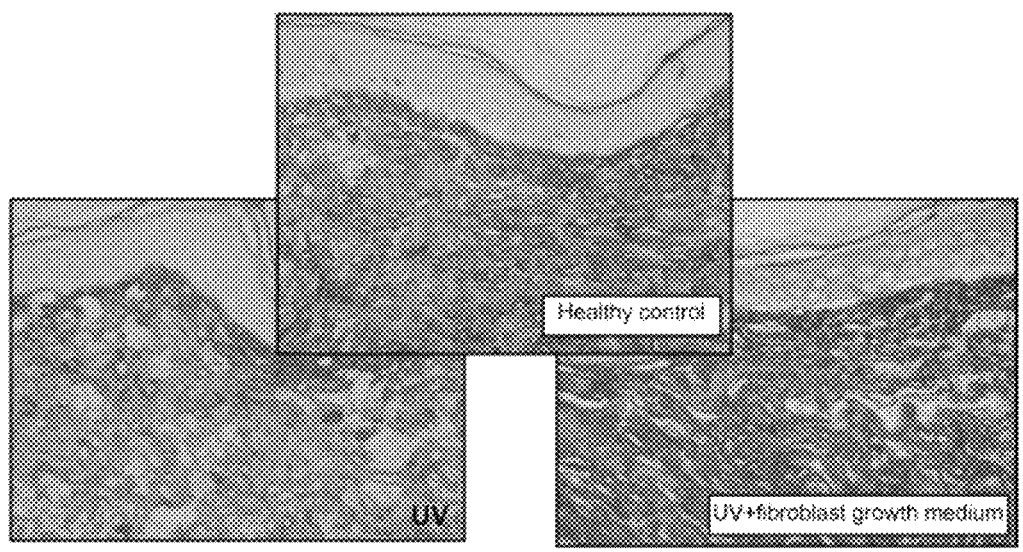

FIG. 3 consists of histological sections showing staining of collagen fibres in healthy skin, in skin altered by irradiation and after treatment with a fibroblast growth medium according to the invention.

Figure 4:
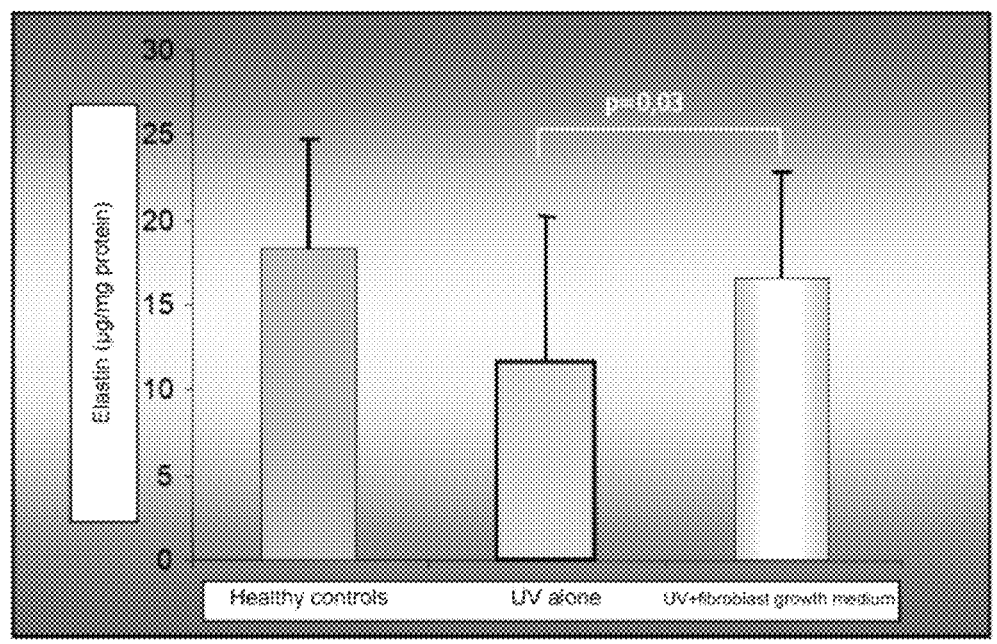

FIG. 4 shows the quantity of elastin in healthy skin, then in skin altered by UV radiation and then after treatment with the fibroblast growth medium according to the invention.

Figure 5:
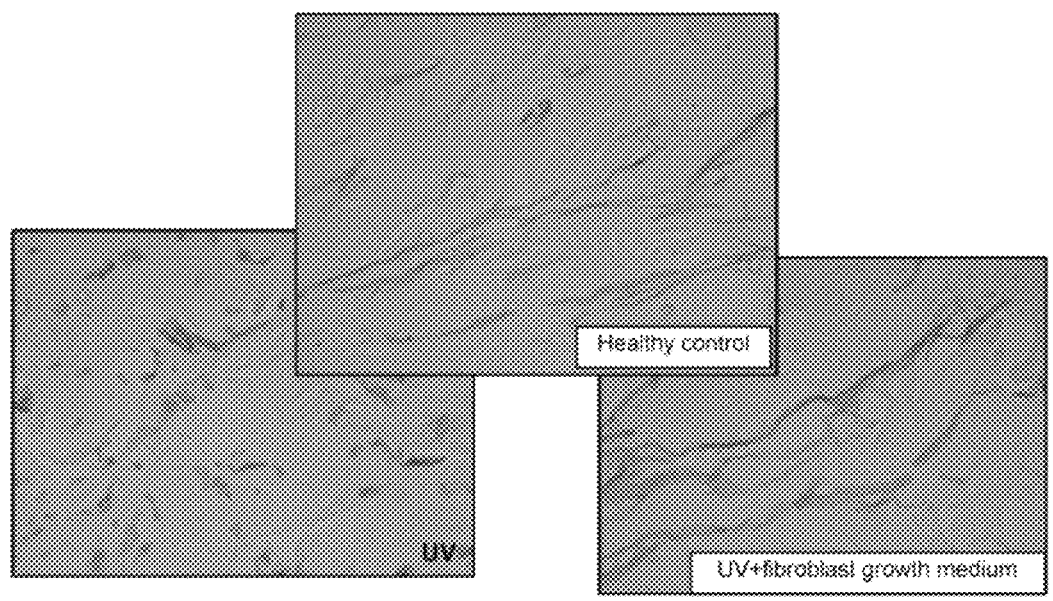

FIG. 5 consists of histological sections showing staining of elastin fibres in healthy skin, in skin altered by irradiation and then treated with the fibroblast growth medium according to the invention.

Figure 6:
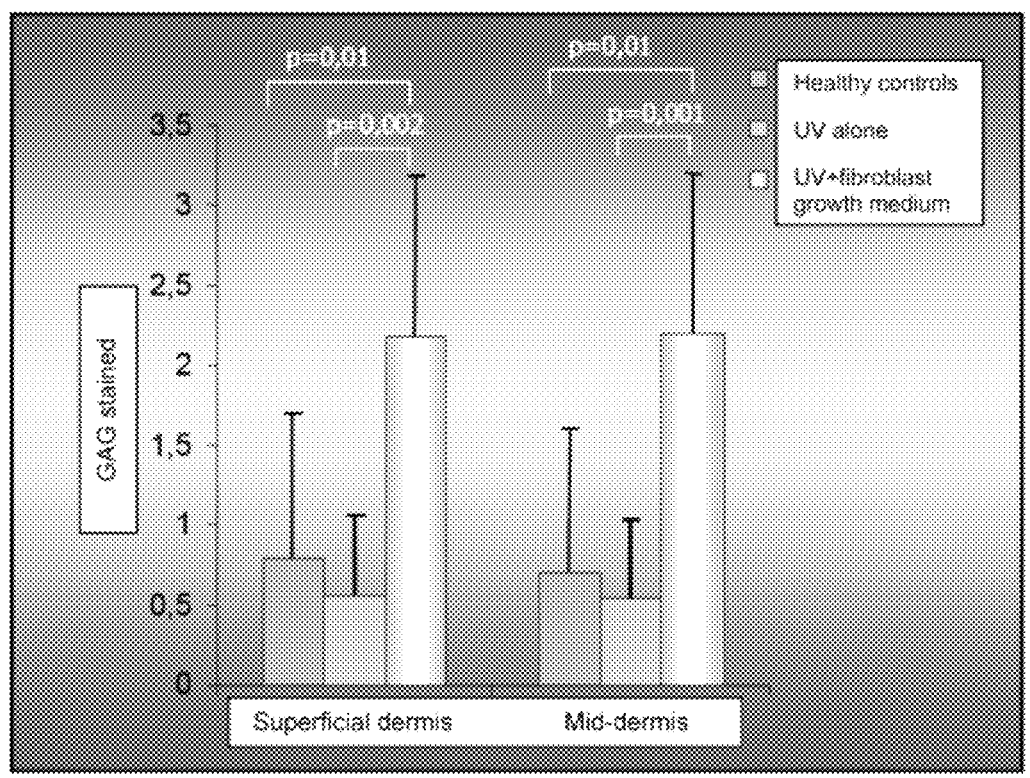

FIG. 6 represents the concentration of GAGs in the superficial and mid-dermis of healthy skin, in skin altered by UV radiation and after treatment with the fibroblast growth medium according to the invention.

Figure 7:
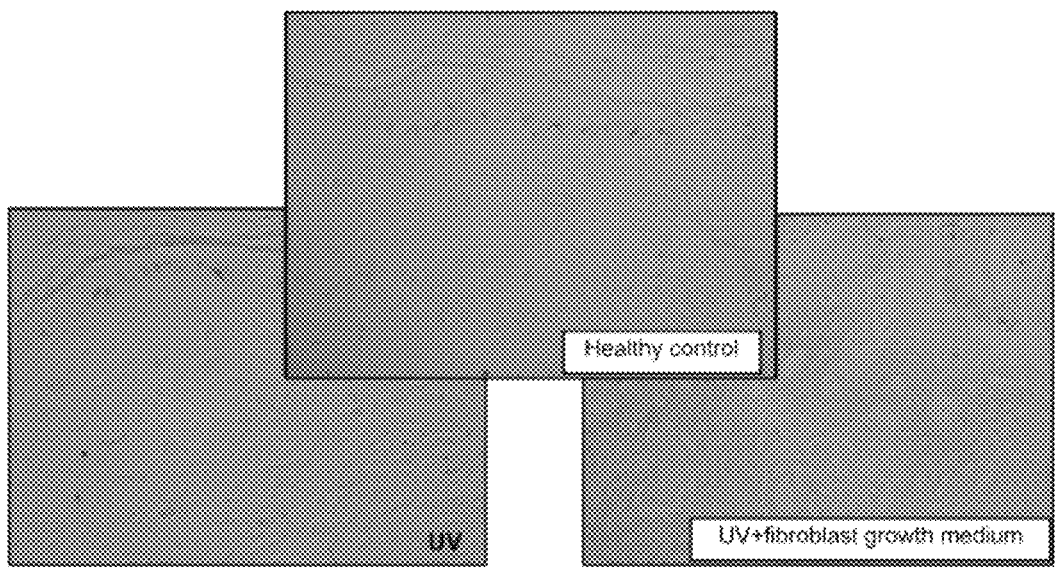

FIG. 7 consists of histological sections showing staining of GAGs in healthy skin, in skin altered by UV irradiation and after treatment with the fibroblast growth medium according to the invention.

EXAMPLES OF EMBODIMENTS

1/ Use of a Fibroblast Growth Medium in an Injectable Composition a) Composition of the Medium:

| NAME ACC. TO THE INTERNATIONAL NOMENCLATURE OF COSMETIC INGREDIENTS (INCI) | FINAL CONCENTRATION Solution 1 X (in mg/l) |
| --- | --- |
| WATER | q.s. 1 litre |
| SODIUM CHLORIDE | 5000 to 8000 |
| L-GLUTAMINE or L-ALANYL-GLUTAMINE | 100 to 3000 |
| SODIUM BICARBONATE | 0 to 2000 |
| D-GLUCOSE | 2000 to 5000 |
| L-ARGININE HCl | 300 to 500 |
| SODIUM ACETATE | 200 to 450 |
| DISODIUM PHOSPHATE $Na_2HPO_4$ | 100 to 1500 |
| L-LEUCINE | 50 to 200 |
| L-SERINE | 50 to 200 |
| MAGNESIUM CHLORIDE $MgCl_2 \cdot 6H_2O$ | 50 to 200 |
| POTASSIUM CHLORIDE | 50 to 200 |
| L-VALINE | 20 to 150 |
| SODIUM PYRUVATE | 10 to 75 |
| L-LYSINE HCl | 10 to 75 |
| L-HISTIDINE HCl·$H_2O$ | 10 to 75 |
| L-CYSTEINE HCl·$H_2O$ | 10 to 75 |
| ADENINE (HCl) | 5 to 50 |
| L-THREONINE | 5 to 50 |
| CALCIUM CHLORIDE $CaCl_2 \cdot 2H_2O$ | 0 to 22.5 |
| MYO-INOSITOL | 5 to 50 |
| L-GLUTAMIC ACID | 15 to 75 |
| L-ASPARAGINE $H_2O$ | 15 to 75 |
| L-METHIONINE | 10 to 50 |
| L-TYROSINE $2Na_2\ 2H_2O$ | 10 to 50 |
| L-PHENYLALANINE | 2 to 20 |
| L-TRYPTOPHAN | 2 to 20 |
| L-ALANINE | 5 to 30 |
| GLYCINE | 5 to 30 |
| L-ISOLEUCINE | 5 to 30 |
| L-ASPARTIC ACID | 10 to 50 |
| SODIUM SULPHATE | 1 to 10 |
| FERROUS SULPHATE $FeSO_4 \cdot 7H_2O$ | 1 to 10 |
| FOLIC ACID | 1 to 5 |
| THYMIDINE | 0.1 to 3 |
| CYANOCOBALAMINE | 0.1 to 3 |
| D-CALCIUM PANTOTHENATE | 1 to 5 |
| THIAMINE HCL | 1 to 5 |
| THIOCTIC ACID | 0.1 to 1 |
| ZINC SULPHATE $ZnSO_4 \cdot 7H_2O$ | 0.05 to 0.5 |
| SODIUM SILICATE $Na_2SiO_3 \cdot 4H_2O$ | 0.05 to 0.5 |
| PYRIDOXINE HCL | 0.5 to 3 |
| NIACINAMIDE (NICOTINAMIDE) | 0.5 to 3 |
| RIBOFLAVIN | 0.05 to 0.5 |
| d-BIOTIN | 0.01 to 0.05 |
| COPPER SULPHATE $CuSO_4 \cdot 5H_2O$ | 0 to 0.005 |
| AMMONIUM MOLYBDATE $(NH4)_6Mo_7O_{24} \cdot 4H_2O$ | 0 to 0.005 |
| AMMONIUM VANADATE $NH_4VO_3$ | 0 to 0.001 |
| MANGANESE CHLORIDE $MnCl_2 \cdot 4H_2O$ | 0 to 0.0001 |
| SODIUM HYALURONATE | 100 to 1000 |
| L-PROLINE | 10 to 100 |
| HYDROXYPROLINE | 10 to 100 |
| ASCORBIC ACID | 0.1 to 10 |
| ADENOSINE | 0.01 to 1 |
| GUANINE | 0.01 to 1 |
| DEOXYRIBOSE | 0.01 to 1 |
| RIBOSE | 0.01 to 1 |
| CHOLINE CHLORIDE | 0 to 3 |
| MPC | 0 to 5000 | b) Human Fibroblast Culture

Protocol

Human fibroblasts were seeded at a low density in 96-well plates in a DMEM standard culture medium, supplemented with FCS (foetal calf serum) cell growth factor. After 24 h, they were cultured in the pure medium according to the invention or in the DMEM standard medium without growth factor.

The media were not renewed during the experiment.

The density of living cells was determined at T0 then after 2, 4, 7 and 9 days, using a colorimetric method (WST-1 reagent).

Results

The culture medium according to the invention alone maintained the growth of the fibroblasts over a period of 9 days. From the 7$^{th}$ day slowing of cell growth was observed which can be explained by the fact that the medium was not renewed (FIG. 1).

Figure 1:
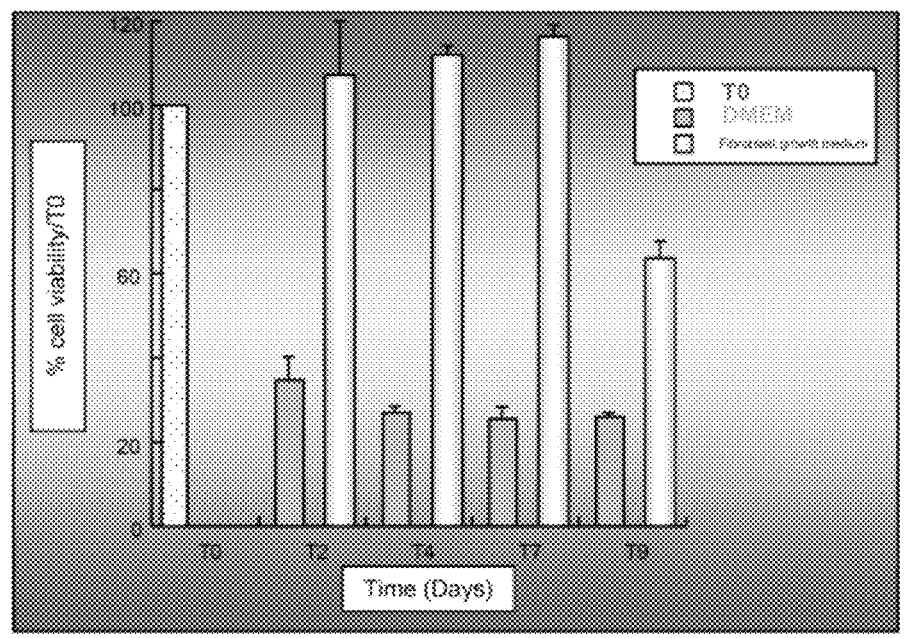
FIG. 1 shows the comparative growth of human fibroblasts in culture in a fibroblast growth medium according to the invention and DMEM standard medium (Sigma), without growth factor.
Figure 2:
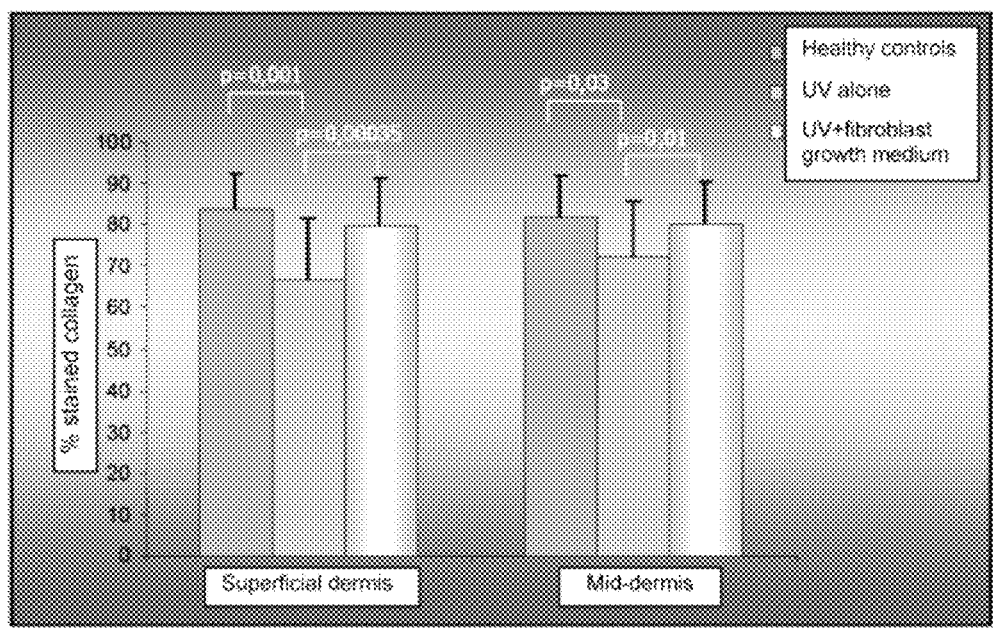
FIG. 2 represents the collagen concentration in the superficial and mid-dermis of healthy skin, in skin altered by UV radiation and after treatment with a fibroblast growth medium according to the invention.

In the DMEM medium without FCS, a reduction in cell viability was seen after 2 days and there was no cell growth throughout the study (FIG. 1).

In conclusion, it appears that the fibroblast growth medium used according to the invention allows survival and stimulates the growth of normal human fibroblasts in the absence of exogenous growth factors.

c) Aiding the Repair of Dermal Components

Protocol

Fragments of skin were taken from 8 donors and put into inserts and placed in culture medium.

Low doses of UVA irradiation were given on D0 and D2 (reduced fibroblast metabolism, alteration to the macromolecules of the connective tissue).

The medium according to the invention was added to the surface of the skin from D3 to D14 (impregnated paper).

Negative controls were made without irradiation (healthy control) or without the application of the medium according to the invention (UV only)

Histological examination (staining):
  Collagen (Sirius red) and elastic fibres (Catechin)>The percentage of the area occupied in the superficial and mid-dermis was assessed (computer assisted image analysis).
  Glycosaminoglycans (GAG) (Hale stain)>Semi-quantitative score (staining intensity).

Biochemical measurement (spectrocolorimetric):
  Total collagen: on fragments of skin after enzyme digestion and homogenization.
  Soluble elastin: in the culture supernatants.
  GAGs: on fragments of homogenized skin.

Results

There was significant reduction in the quantity of collagen and elastin in the superficial and deep dermis following UV irradiation (FIGS. 2 to 5).

There was a statistically significant increase in collagen and elastin staining after treatment with the medium according to the invention (repair of the fibres) (FIGS. 2 to 5).

Fibroblast metabolism was stimulated by the medium according to the invention with significant increase in the concentration of elastin and a tendency towards an increase in collagen (FIGS. 2 to 5).

There was a significantly large increase in the total GAG quantity in the dermis following application of the medium according to the invention (FIGS. 6 and 7).

This model made it possible to quantify the reparative properties on connective tissue of the fibroblast growth medium, on histological sections.

In conclusion, it is apparent that this medium stimulates the repair and restoration of essential components of the dermis (collagen fibres, elastin, GAGs) when tissues have been altered.

2/Preparation of a Gel for Injection for the Treatment of Wrinkles

Fibroblast growth medium.

HA is added up to 3% by weight of the total composition, with preferably: 0.8% for the treatment of superficial wrinkles, 1.6% for the treatment of medium depth wrinkles and 2% for the treatment of deep wrinkles.

Formulation of a gel: The HA is dissolved in the fibroblast culture medium.

The HA concentration determines the viscosity of the final preparation. As an example, the HA used is sodium hyaluronate with a molecular weight between 1.3 and 1.8 MDa. The gel for injection according to the invention does not contain any additive and all the components of the formula act both as excipients and active ingredients.

Sterilization: by 0.22 µm membrane filtration for the fibroblast growth medium, and by separate sterilization of the HA using a process known from the person skilled in the art.

Injection protocol: One or more sessions are envisaged depending on the area to be treated and the depth of the wrinkles. To maintain the results, it may be necessary to repeat the procedure at six monthly intervals, filling the wrinkles lasting longer, the younger the skin.

The invention claimed is:

1. A composition for subcutaneous or intradermal injection consisting of:
  a mechanical filling agent, wherein non-chemically cross-linked hyaluronic acid, or one of its salts, is the mechanical filling agent; and
  a fibroblast growth medium free of fetal calf serum (FCS), wherein the fibroblast growth medium comprises;
  sodium chloride in a final concentration ranging from 5000 to 8000 mg/l;
  L-glutamine or L-alanyl-glutamine in a final concentration ranging from 100 to 3000 mg/l;
  sodium bicarbonate in a final concentration ranging from 0 to 2000 mg/l;
  D-glucose in a final concentration ranging from 2000 to 5000 mg/l;
  L-arginine HCl in a final concentration ranging from 300 to 500 mg/l;
  sodium acetate in a final concentration ranging from 200 to 450 mg/l;
  disodium phosphate (Na$_2$HPO$_4$) in a final concentration ran in from 100 to 1500 mg/L;
  L-leucine in a final concentration ranging from 50 to 200 mg/L;
  L-serine in a final concentration ranging from 50 to 200 mg/L;
  magnesium chloride (MgCl$_2$.6H$_2$O) in a final concentration ranging from 50 to 200 mg/L;
  potassium chloride in a final concentration ranging from 50 to 200 mg/L;
  L-valine in a final concentration ranging from 20 to 150 mg/L;
  sodium pyruvate in a final concentration ranging from 10 to 75 mg/L;
  L-lysine HCl in a final concentration ranging from 10 to 75 mg/L;
  L-histidine HCl H$_2$O in a final concentration ran in from 10 to 75 mg/L;
  L-cysteine HCl H$_2$O in a final concentration ran in from 10 to 75 mg/L;
  adenine HCl in a final concentration ranging from 5 to 50 mg/L;
  L-threonine in a final concentration ranging from 5 to 50 mg/L;
  calcium chloride (CaCl$_2$.2H$_2$O) in a final concentration ran in from 0 to 22.5 mg/L;
  myo-inositol in a final concentration ranging from 5 to 50 mg/L;
  L-glutamic acid in a final concentration ranging from 15 to 75 mg/L;
  L-asparagine H$_2$O in a final concentration ran in from 15 to 75 mg/L;

L-methionine in a final concentration ranging from 10 to 50 mg/L;
L-tyrosine 2Na$_2$.2H$_2$O in a final concentration ran in from 10 to 50 mg/L;
L-phenylalanine in a final concentration ranging from 2 to 20 mg/L;
L-tryptophan in a final concentration ranging from 2 to 20 mg/L;
L-alanine in a final concentration ranging from 5 to 30 mg/L;
glycine in a final concentration ranging from 5 to 30 mg/L;
L-isoleucine in a final concentration ranging from 5 to 30 mg/L;
L-aspartic acid in a final concentration ranging from 10 to 50 mg/l;
sodium sulphate in a final concentration ranging from 1 to 10 mg/l;
ferrous sulphate (FeSO$_4$.7H$_2$O) in a final concentration ran in from 1 to 10 mg/L;
folic acid in a final concentration ranging from 1 to 5 mg/l;
thymidine in a final concentration ranging from 0.1 to 3 mg/l;
cyanocobalamine in a final concentration ranging from 0.1 to 3 mg/l;
d-calcium pantothenate in a final concentration ranging from 1 to 5 mg/l;
thiamine HCl in a final concentration ranging from 1 to 5 mg/L;
thioctic acid in a final concentration ranging from 0.1 to 1 mg/L;
zinc sulphate (ZnSO$_4$.7H$_2$O) in a final concentration ran in from 0.05 to 0.5 mg/L;
sodium silicate (NA$_2$SlO$_3$.4H$_2$O) in a final concentration ran in from 0.05 to 0.5 mg/L;
Pyridoxine HCl in a final concentration ranging from 0.5 to 3 mg/L;
niacinamide (nicotinamide) in a final concentration ranging from 0.5 to 3 mg/L;
riboflavin in a final concentration ranging from 0.05 to 0.5 mg/L;
d-biotin in a final concentration ranging from 0.01 to 0.05 mg/L;
copper sulphate (CuSO$_4$.5H$_2$O) in a final concentration ran in from 0 to 0.005 mg/L;
ammonium molybdate ((NH$_4$)$_6$Mo$_7$O$_{24}$4H$_2$O) in a final concentration ran in from 0 to 0.005 mg/L;
ammonium vanadate (NH$_4$VO$_3$) in a final concentration ran in from 0 to 0.001 mg/L;
manganese chloride (MnCl$_2$.4H$_2$O) in a final concentration ran in from 0 to 0.0001 mg/L;
sodium hyaluronate in a final concentration ranging from 100 to 1000 mg/L;
L-proline in a final concentration ranging from 10 to 100 mg/l;
hydroxyproline in a final concentration ranging from 10 to 100 mg/l;
ascorbic acid in a final concentration ranging from 0.1 to 10 mg/l;
adenosine in a final concentration ranging from 0.01 to 1 mg/l;
guanine in a final concentration ranging from 0.01 to 1 mg/l;
deoxyribose in a final concentration ranging from 0.01 to 1 mg/l;
ribose in a final concentration ranging from 0.01 to 1 mq/l;
choline chloride in a final concentration ranging from 0 to 3 mq/l;
milk peptide complex in a final concentration ranging from 0 to 5000 mg/l; and
water q.s. 1 liter,
wherein the hyaluronic acid or one of its salts forms more than 0.07% of the total mass of the composition.

2. The composition of claim 1, wherein the composition is in the form of a gel.

3. A kit comprising a syringe and the composition of claim 1.

4. A method for filling wrinkles, fine lines, skin depressions and/or scars in a subject comprising the step of administering the composition of claim 1 to the subject.

5. A method for preparing a medicinal product for preventing or treating skin ageing comprising the step of providing the composition of claim 1 and preparing the medicinal product with the composition of claim 1.

6. A cosmetic process for filling wrinkles and/or fine lines comprising the step of injecting at least the composition of claim 1 into the wrinkles and/or the fine lines.

7. A method for preventing or treating wrinkles, fine lines, skin depressions and/or scars in a subject comprising the step of using the composition of claim 1 in the subject as a combination product, wherein the use of the combination product is conducted simultaneously, separately or spread over time.

8. A method for filling wrinkles, fine lines, skin depressions and/or scars comprising the steps of providing the kit of claim 3 and using the composition to fill the wrinkles, fine lines, skin depressions and/or scars.

9. The composition of claim 1, wherein the hyaluronic acid or one of its salts forms more than 0.07 to 3% of the total mass of the composition.

* * * * *